(12) United States Patent
Brown et al.

(10) Patent No.: US 7,429,426 B2
(45) Date of Patent: *Sep. 30, 2008

(54) ORGANOMETALLIC COMPOUNDS FOR USE IN ELECTROLUMINESCENT DEVICES

(75) Inventors: Cory S. Brown, Monroeville, PA (US); David B. Knowles, Apollo, PA (US); Raymond Kwong, Plainsboro, NJ (US); Yeh-Jiun Tung, Princeton, NJ (US); Robert Walters, Export, PA (US); Peter I. Djurovich, Long Beach, CA (US); Mark E. Thompson, Anaheim, CA (US); Bin Ma, Monroeville, PA (US)

(73) Assignees: The University of Southern California, Los Angeles, CA (US); Universal Display Corporation, Ewing, NJ (US)

(*) Notice: Subject to any disclaimer, the term of this patent is extended or adjusted under 35 U.S.C. 154(b) by 594 days.

This patent is subject to a terminal disclaimer.

(21) Appl. No.: 11/002,188

(22) Filed: Dec. 3, 2004

(65) Prior Publication Data
US 2005/0119485 A1    Jun. 2, 2005

Related U.S. Application Data

(63) Continuation of application No. 10/289,915, filed on Nov. 6, 2002, now abandoned.

(51) Int. Cl.
*H01L 51/54* (2006.01)
*C09K 11/06* (2006.01)

(52) U.S. Cl. .................... 428/690; 428/917; 313/504; 313/506; 257/E51.044; 546/4; 546/10

(58) Field of Classification Search .............. None
See application file for complete search history.

(56) References Cited

U.S. PATENT DOCUMENTS

| | | | |
|---|---|---|---|
| 4,769,292 A | 9/1988 | Tang et al. | 428/690 |
| 5,247,190 A | 9/1993 | Friend et al. | 257/40 |
| 5,703,436 A | 12/1997 | Forrest et al. | 313/506 |
| 5,707,745 A | 1/1998 | Forrest et al. | 428/432 |
| 5,834,893 A | 11/1998 | Bulovic et al. | 313/506 |
| 5,844,363 A | 12/1998 | Gu et al. | 313/506 |
| 6,013,982 A | 1/2000 | Thompson et al. | 313/506 |
| 6,087,196 A | 7/2000 | Sturm et al. | 438/29 |
| 6,091,195 A | 7/2000 | Forrest et al. | 313/504 |
| 6,097,147 A | 8/2000 | Baldo et al. | 313/506 |
| 6,294,398 B1 | 9/2001 | Kim et al. | 438/22 |
| 6,303,238 B1 | 10/2001 | Thompson et al. | 428/690 |
| 6,337,102 B1 | 1/2002 | Forrest et al. | 427/64 |
| 6,468,819 B1 | 10/2002 | Kim et al. | 438/22 |
| 7,147,935 B2* | 12/2006 | Kamatani et al. | 428/690 |
| 7,279,232 B2* | 10/2007 | Knowles et al. | 428/690 |
| 2001/0019782 A1 | 9/2001 | Igarashi et al. | 428/690 |
| 2002/0034656 A1 | 3/2002 | Thompson et al. | 428/690 |
| 2003/0059646 A1 | 3/2003 | Kamantani et al. | 428/690 |
| 2003/0068526 A1 | 4/2003 | Kamatani et al. | 428/690 |
| 2003/0068536 A1 | 4/2003 | Tsuboyama et al. | 428/704 |
| 2003/0230980 A1 | 12/2003 | Forrest et al. | 313/600 |
| 2004/0174116 A1 | 9/2004 | Lu et al. | 313/506 |
| 2007/0128466 A1* | 6/2007 | Nomura et al. | 428/690 |

FOREIGN PATENT DOCUMENTS

| | | |
|---|---|---|
| EP | 1 239 526 | 11/2002 |
| WO | 02/15645 | 2/2002 |
| WO | WO 02/44189 | 6/2002 |
| WO | WO 02/066552 | 8/2002 |
| WO | WO 2004/026886 | 4/2004 |

OTHER PUBLICATIONS

M. A. Baldo, et al., "Highly efficient phosphorescent emission from organic electroluminescent devices," Nature, Sep. 1998, vol. 395, pp. 151-154.
M.A. Baldo, et al., "Very high-efficiency green organic light-emitting devices based on electrophosphorescence", Applied Physics Letters, vol. 75, No. 1, pp. 4-6, Jul. 5, 1999.
C. Adachi, et al., "Nearly 100% internal phosphorescence efficiency in an organic light emitting device", J. Appl. Phys. 90, (2001).
Kwong et al., "High operational stability of electrophosphorescent devices", Appl. Phys. Lett., vol. 81, No. 1, pp. 162-164 (Jul. 1, 2002).
J.P.J. Markham, et al., "High-efficiency green phosphorescence from spin-coated single-layer dendrimer light-emitting diodes", Applied Physics Letters, vol. 80, No. 15, pp. 2645-2647, Apr. 15, 2002.
S. Lo, et al., "Green Phosphorescent Dendrimer for Light-Emitting Diodes", Advanced Materials 2002, 14, No. 13-14, pp. 975-979, Jul. 4, 2002.
Shtein et al., U.S. Appl. No. 10/233,470, filed 10/233,470, entitled "Process and Apparatus for Organic Vapor Jet Deposition".

* cited by examiner

*Primary Examiner*—Marie R. Yamnitzky
(74) *Attorney, Agent, or Firm*—Kenyon & Kenyon LLP

(57) ABSTRACT

An organic light emitting device is provided. The device has an anode, a cathode, and an emissive layer disposed between the anode and the cathode. The emissive layer further comprising an emissive material having the structure:

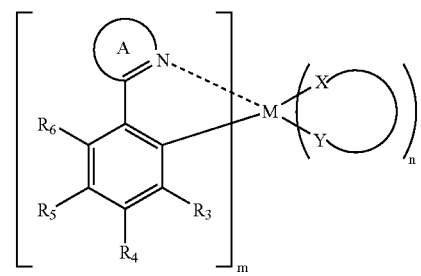

M is a metal having an atomic weight greater than 40. $R_5$ is an aromatic group. The emissive material itself is also provided. The emissive material provides an improved stability and efficiency.

21 Claims, 6 Drawing Sheets

ORGANOMETALLIC COMPOUNDS FOR USE IN ELECTROLUMINESCENT DEVICES

This application is a continuation of U.S. patent application Ser. No. 10/289,915 filed Nov. 6, 2002.

FIELD OF THE INVENTION

The present invention relates to efficient organic light emitting devices (OLEDs), and more specifically to phosphorescent organic materials used in such devices. More specifically, the present invention relates to phosphorescent emitting materials with improved stability and efficiency when incorporated into an OLED.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

Industry standards call for the lifetime of such full color displays to be at least about 5000 hours. In addition, high stability and efficiency are important characteristics of high quality displays. These requirements have helped generate a need for phosphorescent emissive materials that exhibit longer lifetimes, higher stability, and higher efficiency in the red, green and blue wavelength regimes than have been achieved in the prior art.

One example of a green emissive molecule is tris(2-phenylpyridine)iridium, denoted Ir(ppy)$_3$, which has the structure of Formula I:

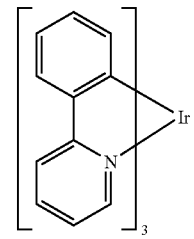

In this, and later figures herein, we depict the dative bond from nitrogen to metal (here, Ir) as a straight line. Ir(ppy)$_3$ emits a spectrum at CIE 0.30, 0.63, and has a stability of about 10,000 hours at an initial photon flux of $2.7 \times 10^{18}$ photon/SR·m$^2$·s, and a quantum efficiency of about 6%. Kwong et al., *Appl. Phys. Lett.*, 81, 162 (2002).

SUMMARY OF THE INVENTION

An organic light emitting device is provided. The device has an anode, a cathode, and an emissive layer disposed between the anode and the cathode. The emissive layer further comprising an emissive material having the structure:

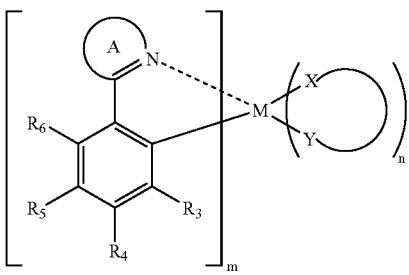

wherein M is a metal having an atomic weight greater than 40;

$R_5$ is a substituent selected from the group consisting of aryl and heteroaryl, wherein said aryl or heteroaryl is unsubstituted or optionally, substituted with non-aromatic groups;

$R_3$ is a substituent selected from the group consisting of H, alkyl, alkenyl, alkynyl, alkylaryl, CN, $CF_3$, $C_nF_{2n+1}$, trifluorovinyl, $CO_2R$, $C(O)R$, $NR_2$, $NO_2$, OR, halo, aryl, heteroary, substituted aryl, substituted heteroaryl or a heterocyclic group;

$R_4$ is a substitutent selected from the group consisting of H, alkyl, alkenyl, alkynyl, alkylaryl, CN, $CF_3$, $C_nF_{2n+1}$, trifluorovinyl, $CO_2R$, $C(O)R$, $NR_2$, $NO_2$, OR, halo, aryl, heteroary, substituted aryl, substituted heteroaryl or a heterocyclic group;

$R_6$ is a substitutent selected from the group consisting of H, alkyl, alkenyl, alkynyl, alkylaryl, CN, $CF_3$, $C_nF_{2n+1}$, trifluorovinyl, $CO_2R$, $C(O)R$, $NR_2$, $NO_2$, OR, halo, aryl, heteroaryl, substituted aryl, substituted heteroaryl or a heterocyclic group;

each R is independently selected from H, alkyl, alkylaryl and aryl;

ring A is an aromatic heterocyclic or a fused aromatic heterocyclic ring with at least one nitrogen atom that is coordinated to the metal M, wherein the ring can be optionally substituted.

(X—Y) is an ancillary ligand;

m is a value from 1 to the maximum number of ligands that may be attached to the metal;

and m+n ≦ the maximum number of ligands that may be attached to the metal.

The emissive material itself is also provided. The emissive material may have improved efficiency and stability when incorporated into a light emitting device. Additionally, the devices of the present invention are expected to exhibit improved quantum efficiency.

DETAILED DESCRIPTION

Figure 1:
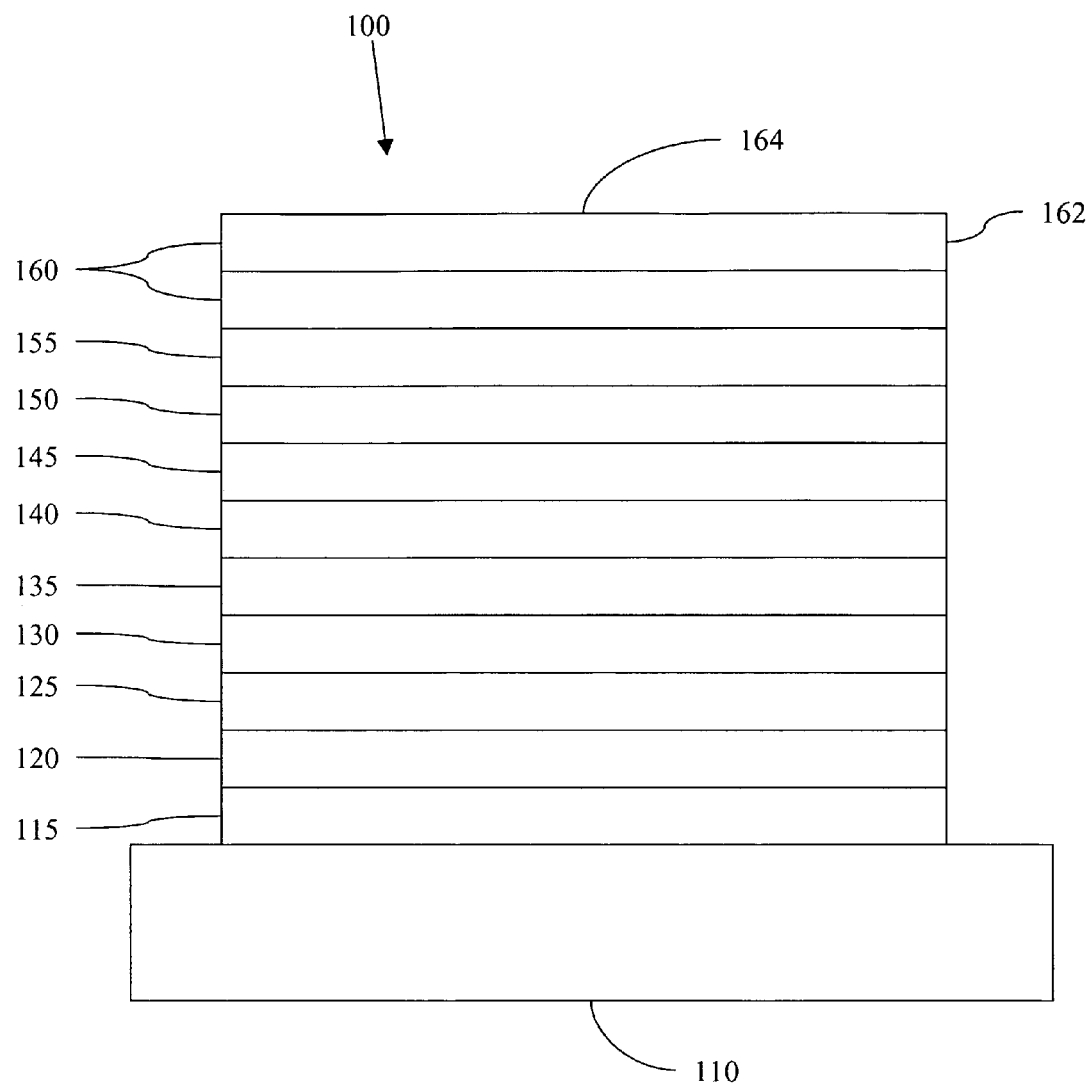
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices", Nature, vol. 395, 151-154, 1998; ("Baldo-I") and Baldo et al., "Very high-efficiency green organic light-emitting devices based on electrophosphorescence", Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that a material that exhibits phosphorescence at liquid nitrogen temperatures may not exhibit phosphorescence at room temperature. But, as demonstrated by Baldo, this problem may be addressed by selecting phosphorescent compounds that do phosphoresce at room temperature.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. No. 5,844,363, which is incorporated by reference in its entirety. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in U.S. patent application Ser. No. 10/173,682 to Forrest et al., which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include Ir(ppy)$_3$. Examples of fluorescent emissive materials include DCM and DMQA. Examples of host materials include Alq$_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer or dendrimer molecule. Other emissive layer materials and structures may be used.

Electron transport layer 140 may include a material capable of transporting electrons. Electron transport layer 140 may be intrinsic (undoped), or doped. Doping may be used to enhance conductivity. Alq$_3$ is an example of an intrinsic electron transport layer. An example of an n-doped electron transport layer is BPhen doped with Li at a molar ratio of 1:1, as disclosed in U.S. patent application Ser. No. 10/173, 682 to Forrest et al., which is incorporated by reference in its entirety. Other electron transport layers may be used.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 140. Blocking layers may also be used to block excitons from diffusing out of the emissive layer. The theory and use of blocking layers is described in more detail in U.S. Pat. No. 6,097,147 and U.S. patent application Ser. No. 10/173,682 to Forrest et al., which are incorporated by reference in their entireties.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
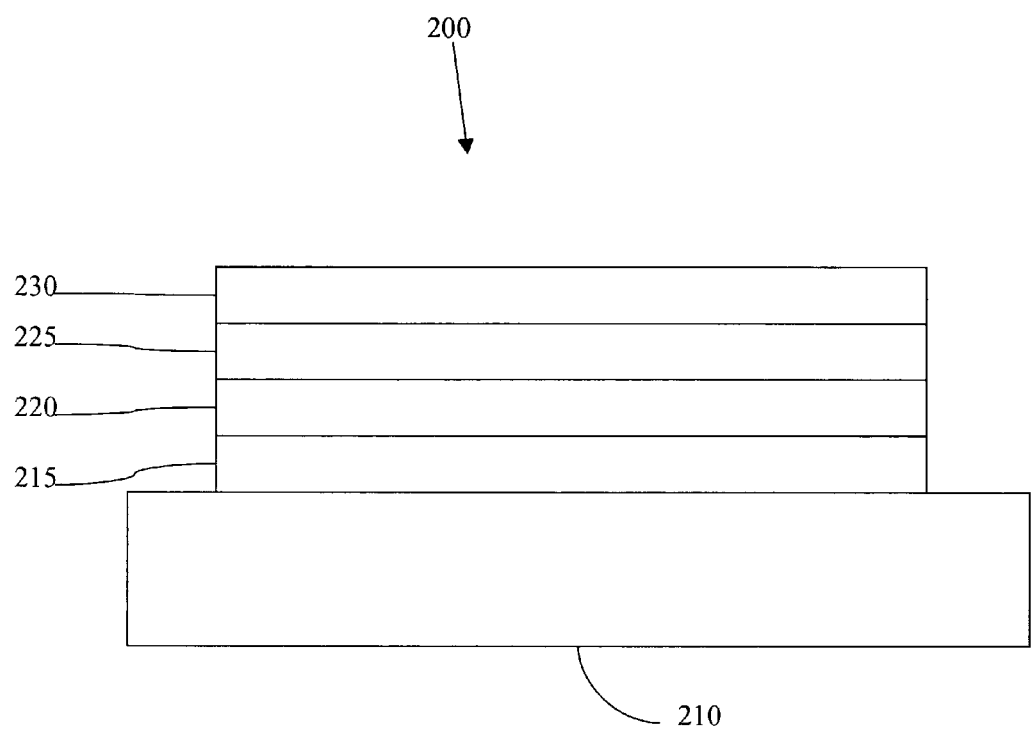
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and organic vapor jet deposition (OVJD), such as described in U.S. patent application Ser. No. 10/233,470, which is incorporated by reference in its entirety. Other suitable deposition methods include spin coating and other solution based processes. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

"Stability" may be measured in a number of ways. One stability measurement is the operational stability of the electroluminescent device. The operational half-life is the time required for the luminance of the device to decay from the initial luminance ($L_0$) to 50% of its initial luminance ($L_{0.5}$) under constant current and at room temperature unless otherwise noted. The devices of the present invention can advantageously have an operational half-life in excess of about 5000 hours.

In an embodiment of the present invention, a phosphorescent emissive material having improved efficiency when incorporated into an organic light emitting device is provided. The emissive material includes a photoactive ligand having the following structure:

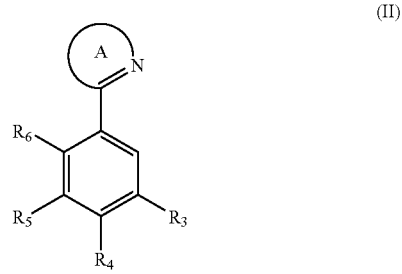

(II)

The substituent $R_5$ is an aryl or a heteroaryl group, which are unsubstituted or optionally, substituted with non-aromatic groups. $R_5$ is preferably substituted or unsubstituted phenyl, naphthyl or pyridyl. $R_5$ is most preferably phenyl. It is believed that an aromatic group at this position on the photoactive ligands advantageously provides greater efficiency when incorporated into an organic light emitting device. Optional substituents on the aryl or heteroaryl group include alkyl, alkenyl, halo, CN, $CF_3$, $C_nF_{2n+1}$, trifluorovinyl, $CO_2R$, C(O)R, $NR_2$, $NO_2$, OR, and heterocyclic groups.

It has been found that the $R_5$ aryl group, if substituted, is advantageously not substituted by an aromatic group. This allows the emissive material comprising a ligand of the formula II to be deposited by vacuum deposition methods when constructing the light emitting device.

The substituents $R_3$, $R_4$ and $R_6$ are independently selected from the group consisting of H, alkyl, alkenyl, alkynyl, alkylaryl, CN, $CF_3$, $C_nF_{2n+1}$, trifluorovinyl, $CO_2R$, C(O)R, $NR_2$, $NO_2$, OR, halo, aryl, heteroaryl, substituted aryl, substituted heteroaryl or a heterocyclic group. Additionally, $R_4$ or $R_6$ may, be combined with a substituent on the $R_5$ aromatic ring to form a bridging group that connects the two rings. Optional bridging groups include —$CH_2$—$CH_2$—, —CH=CH—, —CRR—, —NR—, and —O—.

Ring A is an aromatic heterocyclic ring or a fused aromatic heterocyclic ring with at least one nitrogen atom that is coordinated to the metal M, wherein the ring can be optionally substituted. In a preferred embodiment, A is pyridine, pyrimidine, quinoline, or isoquinoline. Most preferable, A is pyridine. Optional substituents on the Ring A include alkyl, alkenyl, alkynyl, alkylaryl, halo, CN, $CF_3$, $C_nF_{2n+1}$, trifluorovinyl, $CO_2R$, C(O)R, $NR_2$, cyclic-amino, $NO_2$, and OR. Additionally, a substituent on ring A and $R_6$ may be combined to form an ethylene (—$CH_2$—$CH_2$—) or a —CH=CH— group that connects the two rings.

Each R is independently selected from H, alkyl, alkylaryl and aryl.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, $CO_2R$, C(O)R, $NR_2$, cyclic-amino, $NO_2$, and OR.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted with one or more substituents selected from halo, CN, $CO_2R$, C(O)R, $NR_2$, cyclic-amino, $NO_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, $CO_2R$, C(O)R, $NR_2$, cyclic-amino, $NO_2$, and OR.

The term "alkynyl" as used herein contemplates both straight and branched chain alkyne radicals. Preferred alkyl groups are those containing two to fifteen carbon atoms. Additionally, the alkynyl group may be optionally substituted with one or more substituents selected from halo, CN, $CO_2R$, C(O)R, $NR_2$, cyclic-amino, $NO_2$, and OR.

The terms "alkylaryl" as used herein contemplates an alkyl group which has as a substituent an aromatic group. Additionally, the alkylaryl group may be optionally substituted on the aryl with one or more substituents selected from halo, CN, $CO_2R$, C(O)R, $NR_2$, cyclic-amino, $NO_2$, and OR.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like.

The term "aryl" or "aromatic group" as used herein contemplates single-ring aromatic groups and polycyclic ring systems. The polycyclic rings may have two or more rings in which two carbons are common by two adjoining rings (the rings are "fused") wherein at least one of the rings is aromatic, e.g., the other rings can be cycloalkyls, cycloalkenyls, aryl, heterocycles and/or heteroaryls.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls.

All value ranges, for example those given for n and m, are inclusive over the entire range. Thus, for example, a range between 0-4 would include the values 0, 1, 2, 3 and 4.

This ligand is referred to as "photoactive" because it is believed that it contributes to the photoactive properties of the emissive material. The emissive material comprises at least one photoactive ligand of the formula II and a heavy metal ion such that the resulting material has (i) a carbon-metal bond and (ii) the nitrogen of ring A is coordinated to the metal. Thus the emissive materials of the present invention comprise a partial structure of formula (III)

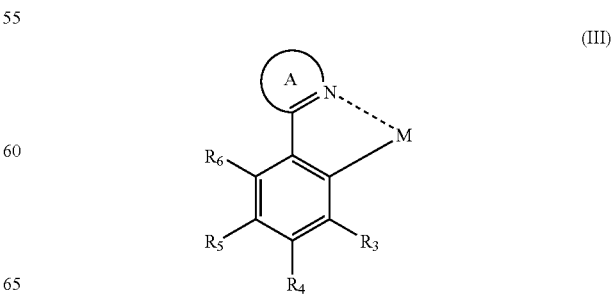

(III)

M may be any metal having an atomic weight greater than 40. Preferred metals include Ir, Pt, Pd, Rh, Re, Os, Ti, Pb, Bi, In, Sn, Sb, Te, Au, and Ag. More preferably, the metal is Ir or Pt. Most preferably, the metal is Ir.

In another embodiment of the invention, the emissive material has the Formula IV:

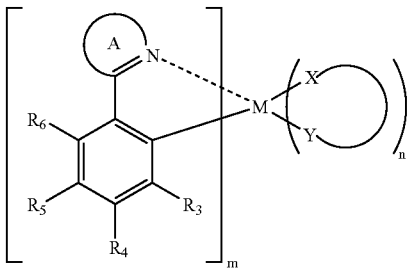

m, the number of photoactive ligands of a particular type, may be any integer from 1 to the maximum number of ligands that may be attached to the metal. For example, for Ir, m may be 1, 2 or 3. n, the number of "ancillary" ligands of a particular type, may be any integer from zero to one less than the maximum number if ligands that may be attached to the metal. (X—Y) represents an ancillary ligand. These ligands are referred to as "ancillary" because it is believed that they may modify the photoactive properties of the molecule, as opposed to directly contributing to the photoactive properties. The definitions of photoactive and ancillary are intended as non-limiting theories. For example, for Ir, n may be 0, 1 or 2 for bidentate ligands. Ancillary ligands for use in the emissive material may be selected from those known in the art. Non-limiting examples of ancillary ligands may be found in PCT Application Publication WO 02/15645 A1 to Lamansky et al. at pages 89-90, which is incorporated herein by reference. Preferred ancillary ligands include acetylacetonate (acac) and picolinate (pic), and derivatives thereof. The preferred ancillary ligands have the following structures:

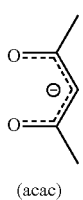 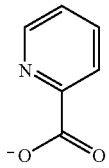
(acac) (pic)

In a preferred embodiment, the ring A of the photoactive ligand is pyridine, giving a ligand of the formula $II_a$:

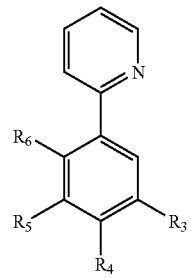

and a partial structure for the emissive material of the formula $III_a$:

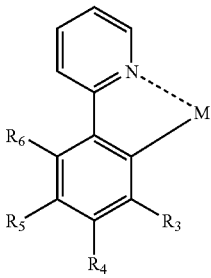

The emissive material of this embodiment has the following structure of Formula $IV_a$:

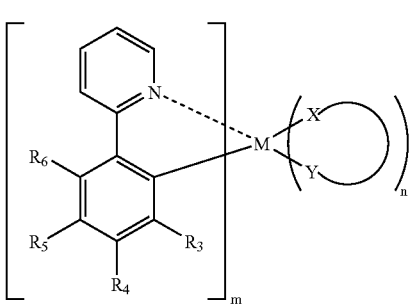

In the structures $II_a$, $III_a$ and $IV_a$, the pyridine ring may be optionally substituted.

In another preferred embodiment, the substituent $R_5$ of the photoactive ligand is phenyl, giving a ligand of the formula $II_b$:

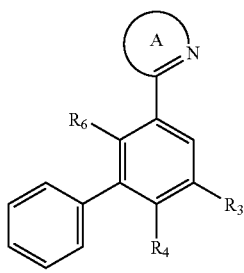

and a partial structure for the emissive material of the formula $III_b$:

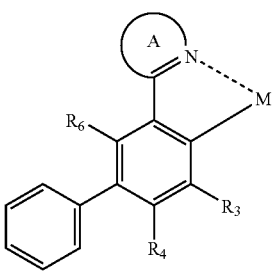

(III$_b$)

The emissive material of this embodiment has the following structure of formula IV$_b$:

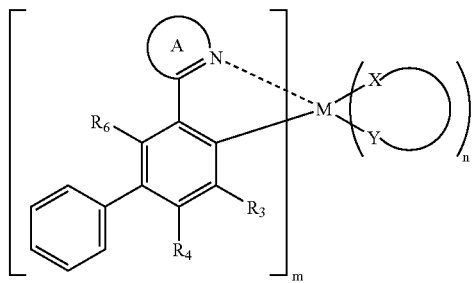

(IV$_b$)

In the structures II$_b$, III$_b$ and IV$_b$, the phenyl substitutent may be optionally substituted.

In another preferred embodiment, n is zero, and m is the maximum number of ligands that may be attached to the metal.

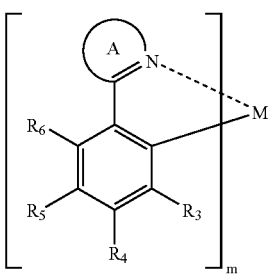

(V)

For example, for Ir, m is three in this preferred embodiment, and the structure may be referred to as a "tris" structure. The tris structure is preferred because it is believed to be particularly stable.

In one embodiment, m+n is equal to the total number of bidentate ligands that may be attached to the metal in question—for example, 3 for Ir. In another embodiment, m+n may be less than the maximum number of bidentate ligands that may be attached to the metal, in which case other ligands—ancillary, photoactive, or otherwise—may also be attached to the metal. Preferably, if there are different photoactive ligands attached to the metal, each photoactive ligand has the structure indicated in Formula II.

In another embodiment of the present invention, M is Ir and m is 3, giving an emissive material of the formula

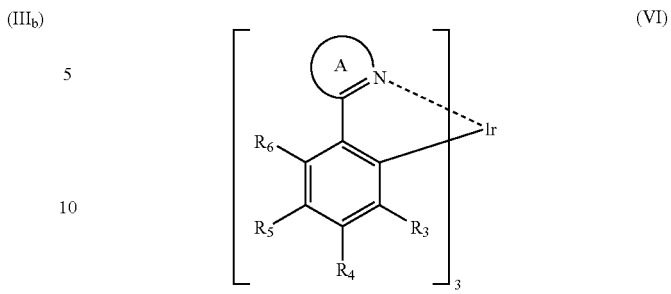

(VI)

In a most preferred embodiment, referred to herein as "Compound 1", M is Ir, R$_5$ is phenyl, R$_3$=R$_4$=R$_6$=H and ring A is pyridine. The emissive material of this embodiment has the following structure of Formula VII:

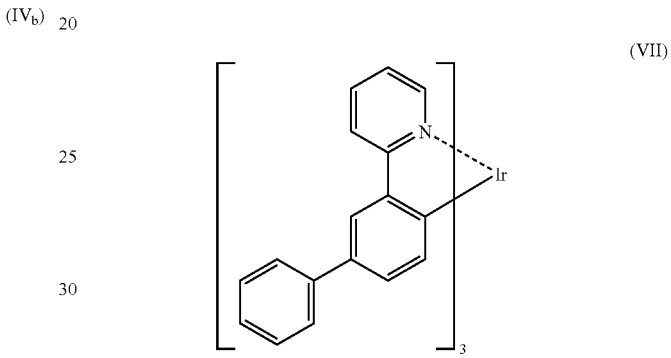

(VII)

The devices of the present invention show an improvement over those in the prior art utilizing, for example, Ir(ppy)$_3$. For example, luminescent efficiency of devices made according to the present invention show about 8% increase in efficiency over Ir(ppy)$_3$ devices, while maintaining equivalent or longer operational lifetimes.

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

Material Definitions:

As used herein, abbreviations refer to materials as follows:

| | |
|---|---|
| CBP: | 4,4'-N,N'-dicarbazole-biphenyl |
| m-MTDATA | 4,4',4''-tris(3-methylphenylphenlyamino)triphenylamine |
| Alq$_3$: | 8-tris-hydroxyquinoline aluminum |
| BPhen: | 4,7-diphenyl-1,10-phenanthroline |
| n-BPhen: | n-doped BPhen (doped with lithium) |
| F$_4$-TCNQ: | tetrafluoro-tetracyano-quinodimethane |
| p-MTDATA: | p-doped m-MTDATA (doped with F4-TCNQ) |
| Ir(ppy)$_3$: | tris(2-phenylpyridine)-iridium |
| Ir(ppz)$_3$: | tris(1-phenylpyrazoloto,N,C(2')iridium(III) |
| BCP: | 2,9-dimethyl-4,7-diphenyl-1,10-phenanthroline |
| TAZ: | 3-phenyl-4-(1'-naphthyl)-5-phenyl-1,2,4-triazole |
| CuPc: | copper phthalocyanine. |
| ITO: | indium tin oxide |
| NPD: | naphthyl-phenyl-diamine |
| TPD: | N,N'-bis(3-methylphenyl)-N,N'-bis-(phenyl)-benzidine |

-continued

| | |
|---|---|
| BAlq: | aluminum(III)bis(2-methyl-8-quinolinato)4-phenylphenolate |
| mCP: | 1,3-dicarbazole-benzene |
| DCM: | 4-(dicyanomethylene)-6-(4-dimethylaminostyryl-2-methyl)-4H-pyran |
| DMQA: | N,N'-dimethylquinacridone |

EXAMPLES

Specific representative embodiments of the invention will now be described, including how such embodiments may be made. It is understood that the specific methods, materials, conditions, process parameters, apparatus and the like do not necessarily limit the scope of the invention.

Example 1

Synthesis of Tris(2-[3-biphenyl]pyridine)Iridium (III) (Compound 1)

Step 1

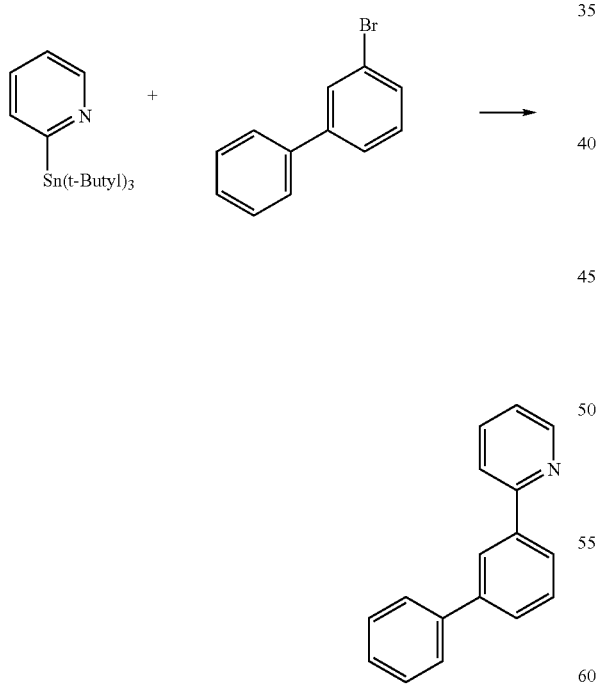

3-Bromobiphenyl (3.0 g, 12.9 mmol) 2-tributylstannylpyridine (5.92 g, 16.1 mmol) and dichlorobis(triphenylphosphine)palladium (II) (0.45 g) were refluxed in 75 mL of o-xylene under a stream of $N_2$ gas for 20 hours. The crude material was then purified on silica gel using 20% EtOAc/Hexanes. The pure fractions were evaporated of solvent to give 2-(3-biphenyl)pyridine (2.90 g, 97.6 % yield) as a yellow oil.

Step 2

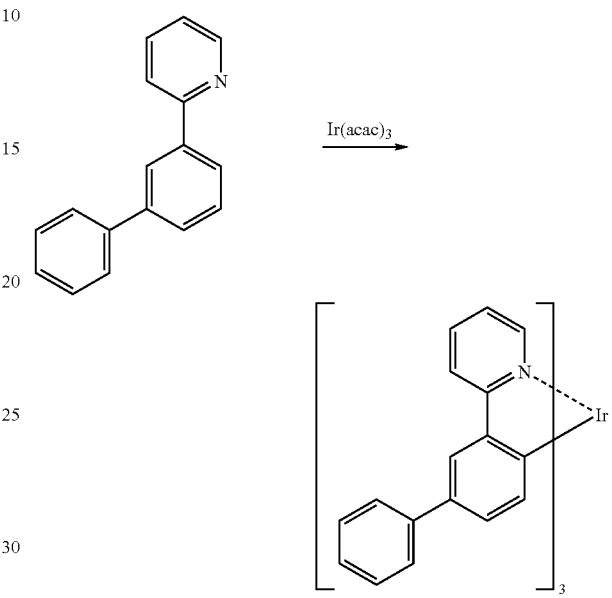

2-(3-Biphenyl)pyridine (2.90 g, 13.5 mmol) and iridium (III) acetylacetonate (1.24 g, 2.51 mmol) were refluxed in 50 mL glycerol under a stream of $N_2$ gas for 48 hours. The mixture was then cooled, enriched with $MeCl_2$ and extracted twice from brine. The organic layer was dried over anhydrous $MgSO_4$, filtered and dried on silica. The silica layer was then added to a silica gel column that was prepared with 40% EtOAc/Hexanes. Impurities were removed by elution with 40% EtOAc/Hexanes. After all impurities were removed, the column was flushed with $MeCl_2$ to obtain the desired product. Evaporation of solvent afforded 1.80 g solid (81.8% yield). Further purification was achieved by dissolving the solid in a minimal amount of $MeCl_2$ and recrystallizing from Toluene. 1.0 g of this material was successfully sublimed to give tris (2-[3-biphenyl]pyridine) Iridium (III) (0.43 g).

Example 2

Experimental Device Fabrication

The starting substrates were glass substrates coated with ITO of 130-150 nm thickness and sheet resistance <20 Ω/square, purchased from Applied Films Corporation of Longmont, Colo. The substrates were degreased with solvents and cleaned with oxygen plasma and UV ozone treatments. All subsequent thin films were deposited by thermal evaporation at a pressure of $<1\times10^{-6}$ Torr. First CuPc was deposited as a hole injection layer on the anode to a thickness of 10 nm at a rate of 0.3 Å/s. Next, NPD was deposited as a hole transport layer to a thickness of 30 nm at a rate of 1.5 Å/s. Next, CBP and an emitting material, such as Compound 1 or Ir(ppy)$_3$, were co-evaporated from different sources to form a light emitting layer of 30 nm thickness. CBP was deposited at a rate of 1.6 Å/s, and the emissive dopant was incorporated at a concentration of 4.5 wt %. Next, on the light emitting layer, BAlq was deposited as a hole blocking layer to a thickness of 10 nm at a rate of 1.0 Å/s. Next, on the hole blocking layer, $Alq_3$ was deposited as an electron transporting layer to a thickness of 30 nm at a rate of 1.0 Å/s. Next, on the electron transport layer, lithium fluoride (LiF) was deposited as an electron injecting layer at a thickness of 0.5 nm at a rate of 0.5 Å/s. Lastly, aluminum (Al) was deposited on the electron injecting layer at a thickness of 100 nm at a rate of 2 Å/s to complete the organic light emitting device.

The devices were characterized by measuring current-voltage and luminance characteristics, as well as spectral output characteristics. The external quantum efficiency was determined as a function of current density. Device stability was characterized by measuring the device luminance as a function of time under constant current drive. Stability was measured at an initial luminance of 600 cd/m$^2$, or $3.3 \times 10^{18}$ photos/SR·m$^2$·s.

Figure 3:
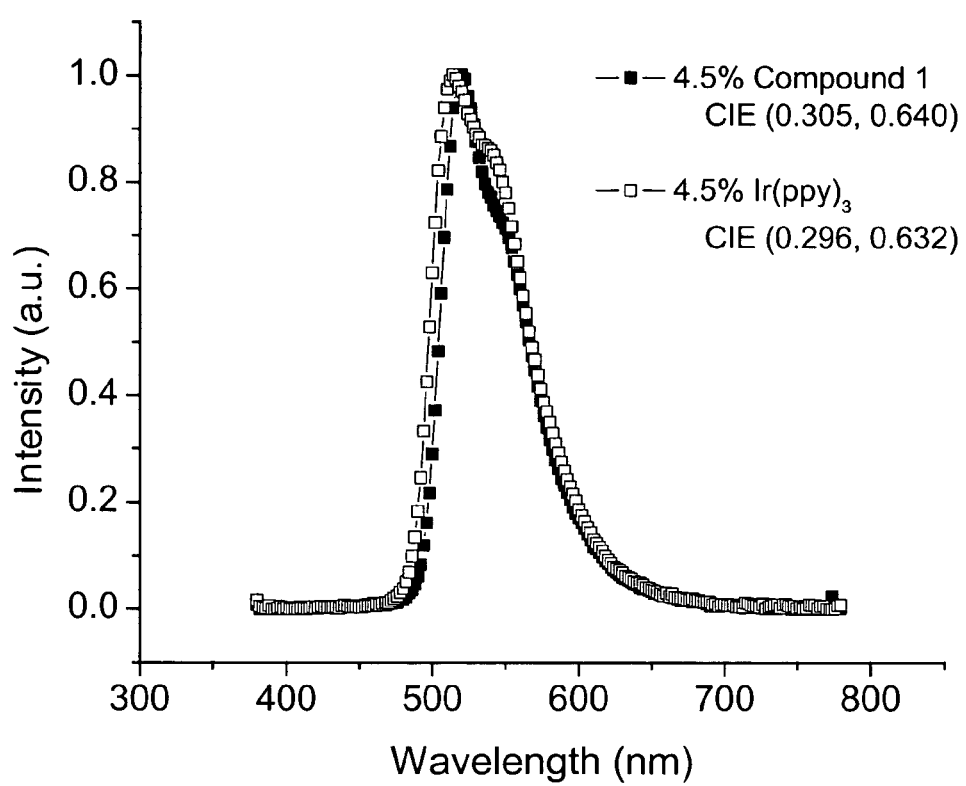
FIG. 3 shows the normalized spectra of a Compound 1 device and an $Ir(ppy)_3$ device.

FIG. 3 shows the normalized spectra of a Compound 1 device and an Ir(ppy)$_3$ device. The CIE of the disclosed compound is (0.305, 0.640) at 10 mA/cm$^2$, compared to Ir(ppy)$_3$ CIE coordinates of (0.30, 0.63).

Figure 4:
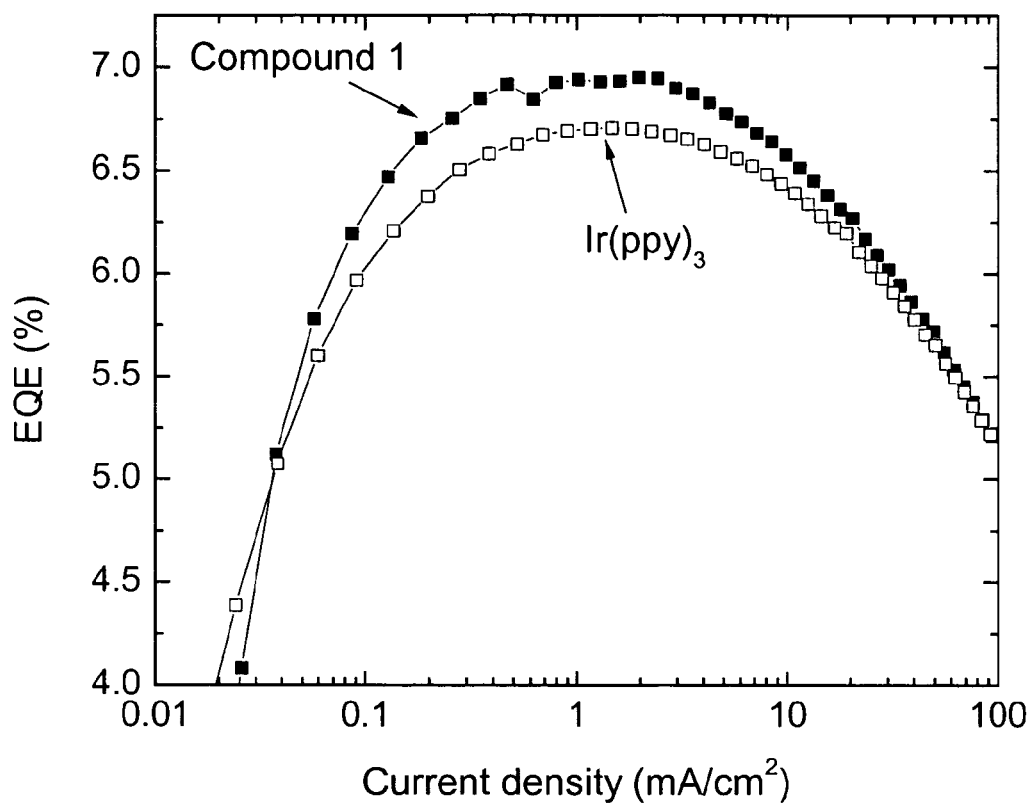
FIG. 4 shows the external quantum efficiency of a device using Compound 1 as the emissive material doped at 4.5 wt % compared with a device using $Ir(ppy)_3$ as the emissive material doped at 4.5 wt %.

FIG. 4 shows the external quantum efficiency of a device using Compound 1 as a dopant at 4.5 wt % compared with a device using Ir(ppy)$_3$ as a dopant at 4.5 wt %. Without being limited by a theory, it is believed that incorporating an aromatic group at the R$_5$ position increases the π-conjugation of the material. In t-conjugated organic materials, increased π-conjugation is generally accompanied by an enhancement in the PL efficiency and a slight bathochromic shift (red shift) of the emission. The increase in PL efficiency may translate in an increase in the EL efficiency in an electroluminescent device. Compound 1 has a phenyl substituent in the R$_5$ position. This extends the π-conjugation over the Ir(ppy)$_3$ molecule which is unsubstituted. The electroluminescence of the Compound 1 device is indeed slightly red-shifted, with an emission maximum of 519 nm compared to 514 nm of Ir(ppy)$_3$ device. The compound 1 device also demonstrates a higher external quantum efficiency (EQE), with a maximum of 7.0% EQE compared to 6.5% EQE of the Ir(ppy)$_3$ device.

Figure 5:
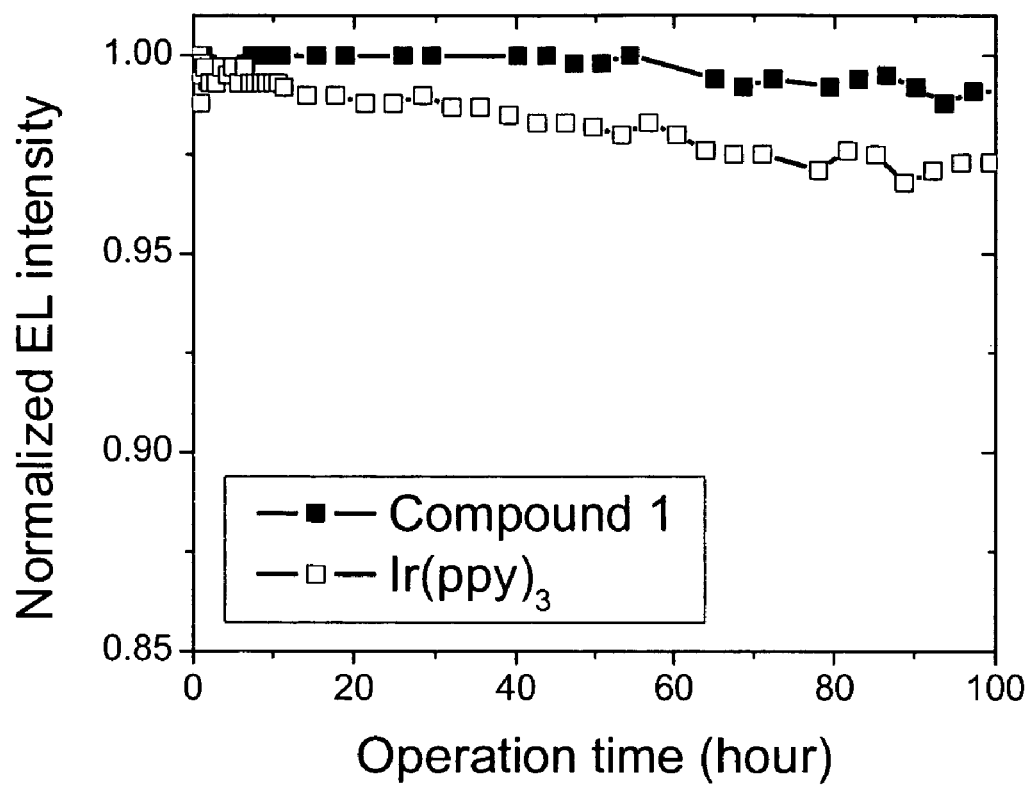
FIG. 5 shows the normalized luminance decay for Compound 1 and $Ir(ppy)_3$ devices under constant current drive.
Figure 6:
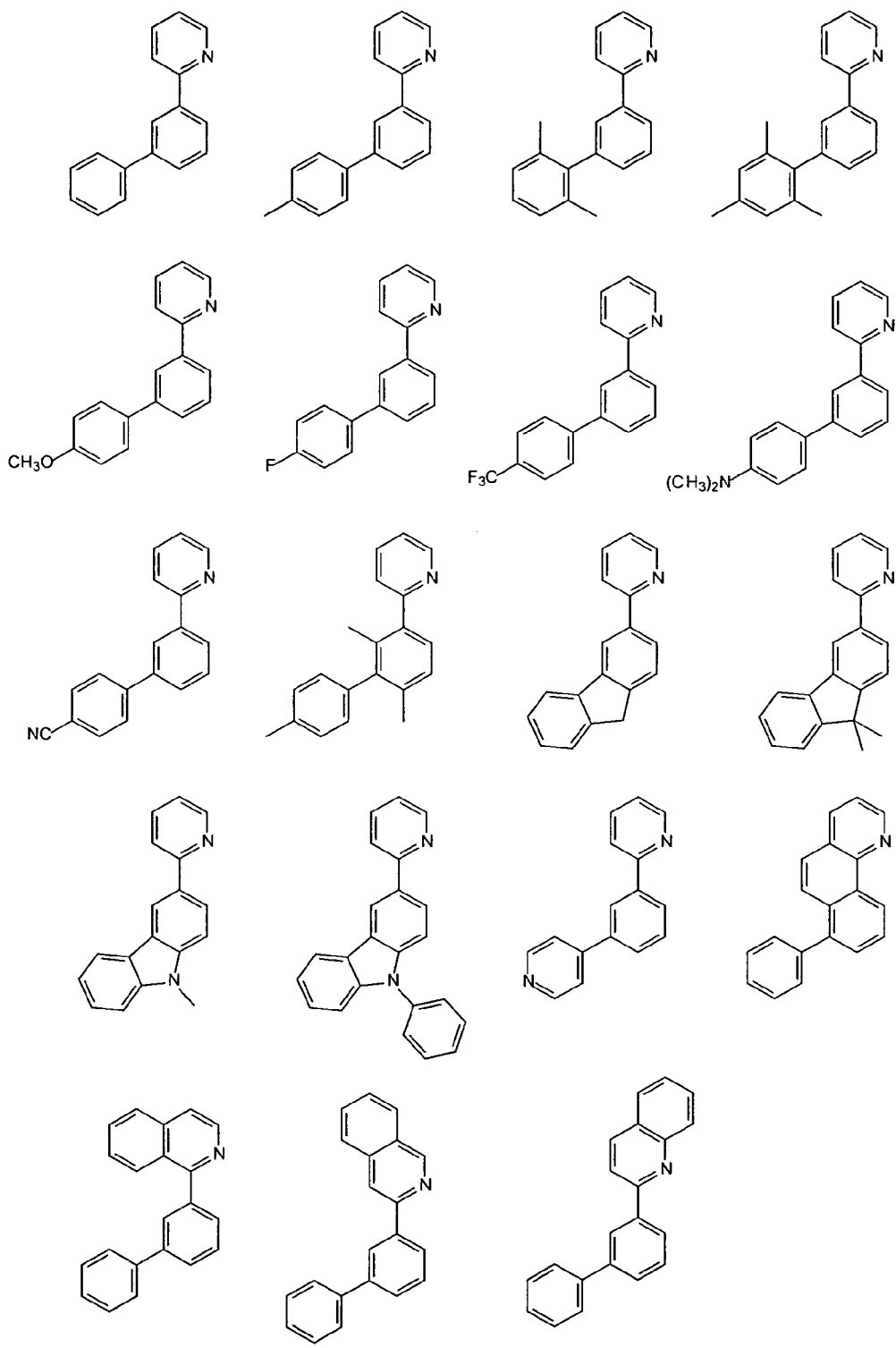
FIG. 6 shows the chemical structures of representative photoactive ligands.

FIG. 5 shows the operational stability of the devices using Compound 1 and Ir(ppy)$_3$ as the emitting materials to 100 hours under constant current drive. The improved stability of the Compound 1 device can be seen. After 100 hours of continuous operation under constant current drive at an initial luminance of 600 cd/m$^2$ or $3.3 \times 10^{18}$ photon/sr·m$^2$·s at room temperature, the luminance is retained at 99% and 97% for the Compound 1 and Ir(ppy)$_3$ devices respectively. This seemingly small increase at this early time of operation can result in a large in half-life.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

What is claimed is:
1. An emissive material comprising a ligand having the structure:

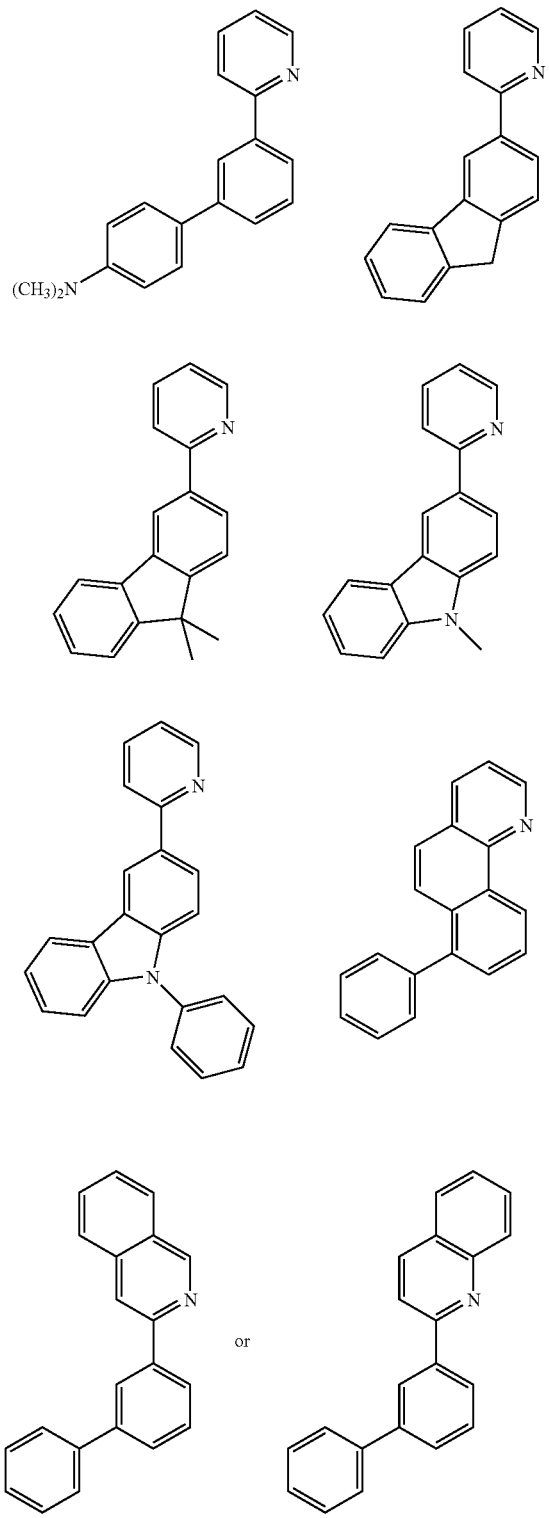

wherein the ligand is attached to a metal having an atomic weight greater than 40.

2. The emissive material of claim 1 comprising a ligand having the structure:

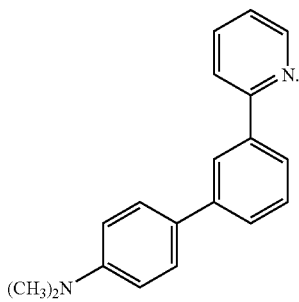

3. The emissive material of claim 1 comprising a ligand having the structure:

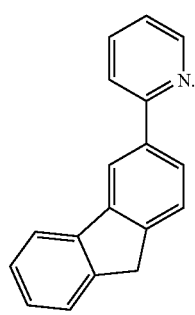

4. The emissive material of claim 1 comprising a ligand having the structure:

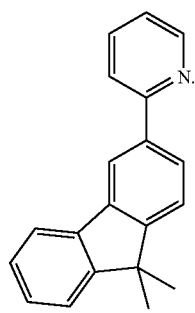

5. The emissive material of claim 1 comprising a ligand having the structure:

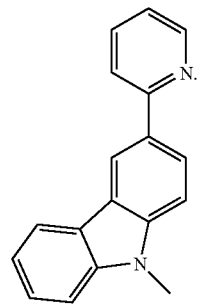

6. The emissive material of claim 1 comprising a ligand having the structure:

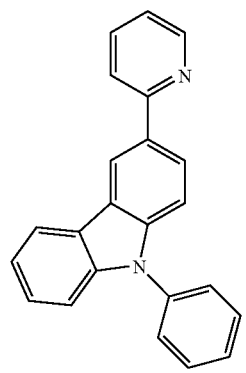

7. The emissive material of claim 1 comprising a ligand having the structure:

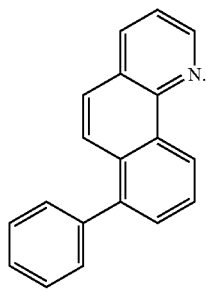

8. The emissive material of claim 1 comprising a ligand having the structure:
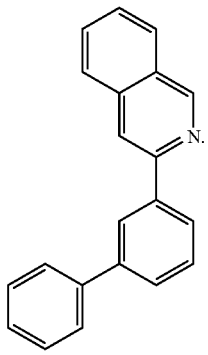
9. The emissive material of claim 1 comprising a ligand having the structure:
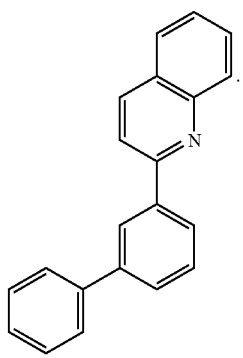
10. An emissive material comprising the structure:
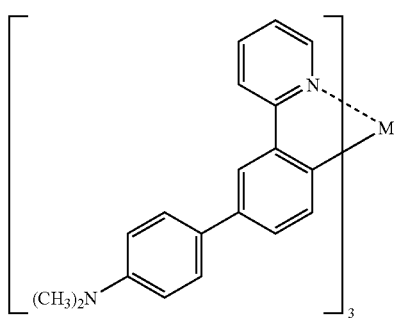
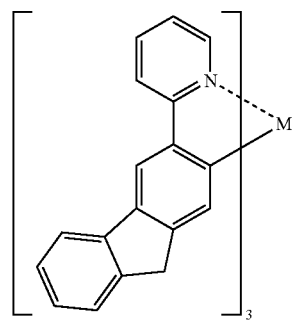
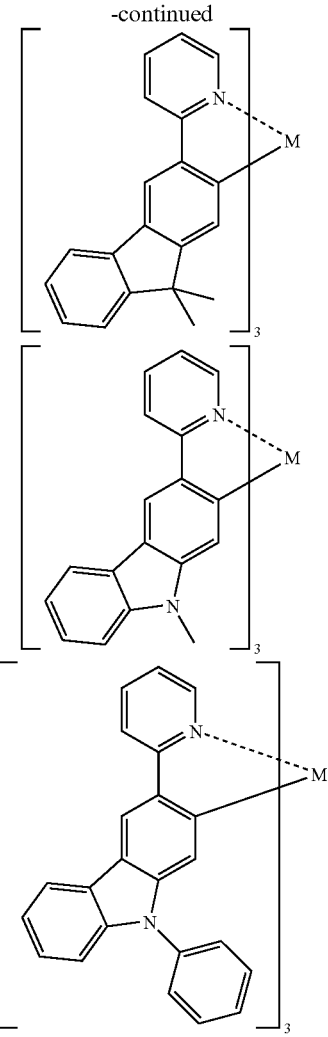
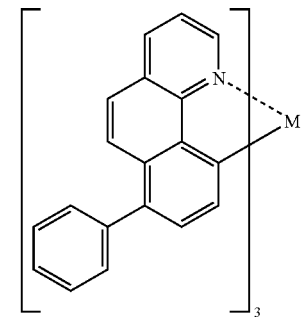
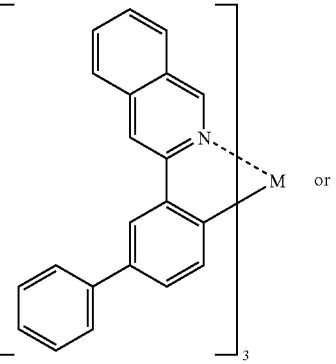 or -continued

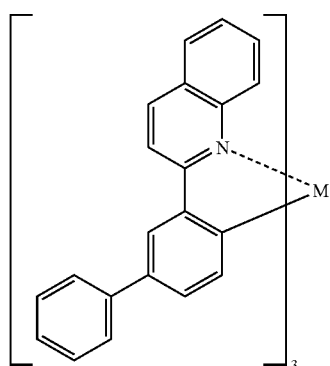

wherein M is a metal having an atomic weight greater than 40.

11. The emissive material of claim 10 comprising the structure:

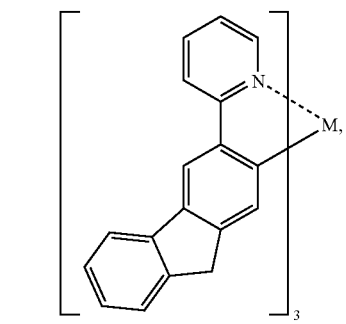

wherein M is iridium.

12. The emissive material of claim 10 comprising the structure:

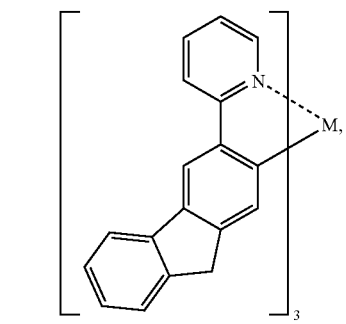

wherein M is iridium.

13. The emissive material of claim 10 comprising the structure:

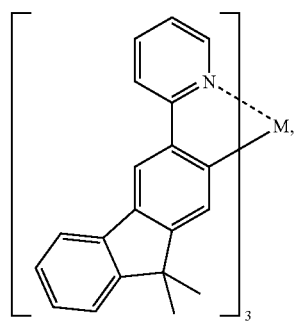

wherein M is iridium.

14. The emissive material of claim 10 comprising the structure:

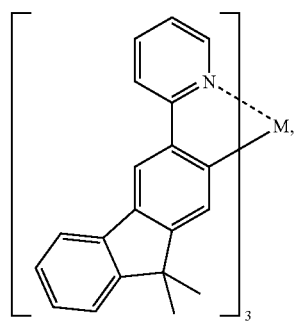

wherein M is iridium.

15. The emissive material of claim 10 comprising the structure:

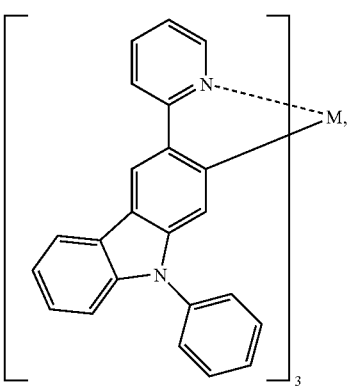

wherein M is iridium.

16. The emissive material of claim 10 comprising the structure:

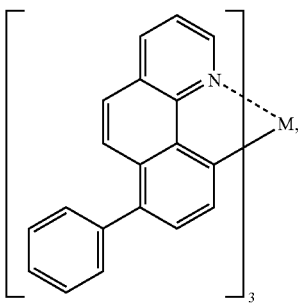

wherein M is iridium.

17. The emissive material of claim 10 comprising the structure:

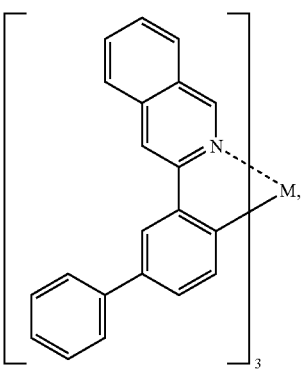

wherein M is iridium.

18. The emissive material of claim 10 comprising the structure:

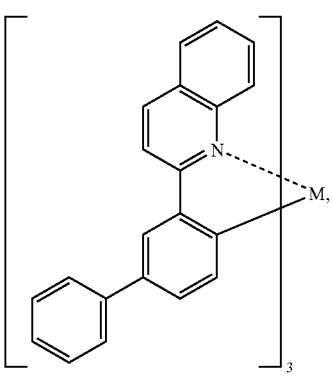

wherein M is iridium.

19. An organic light emitting device, comprising:
(a) an anode;
(b) a cathode;
(c) an emissive layer disposed between the anode and the cathode, the emissive layer comprising an emissive material comprising a ligand having the structure:

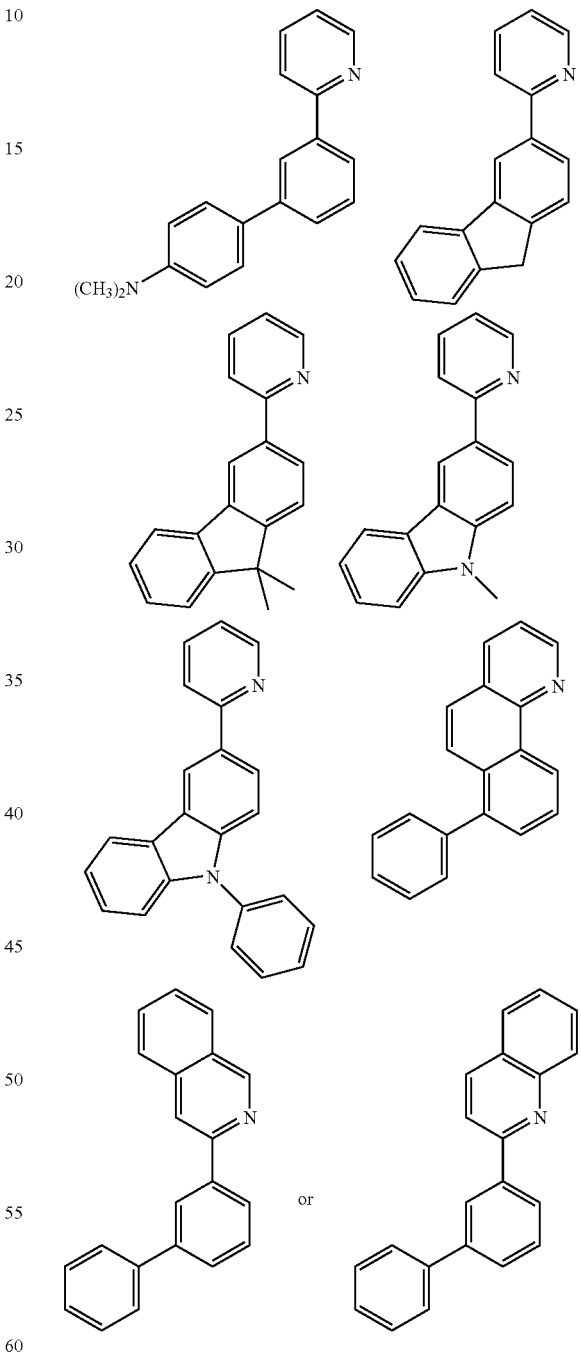

wherein the ligand is attached to a metal having an atomic weight greater than 40.

20. An organic light emitting device, comprising:
(a) an anode;
(b) a cathode;

(c) an emissive layer disposed between the anode and the cathode, the emissive layer comprising an emissive material having the structure:
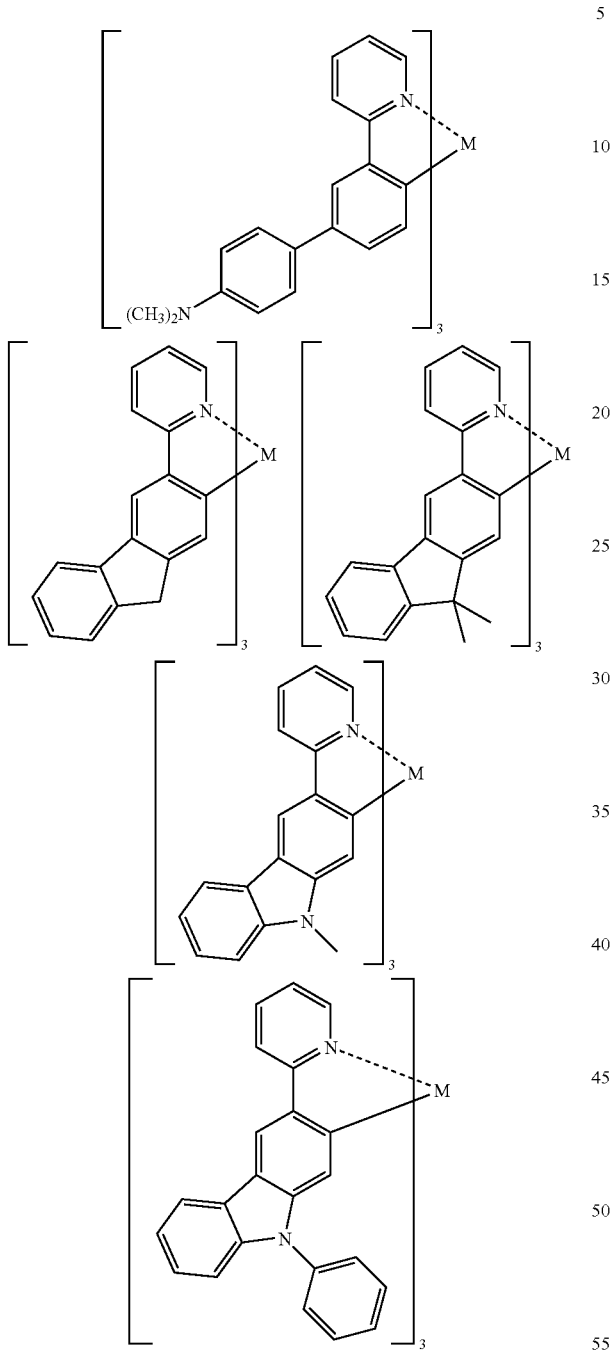
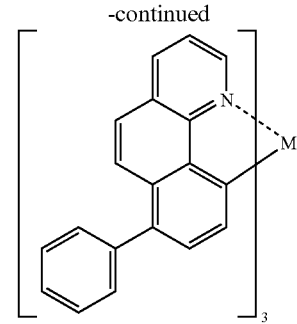
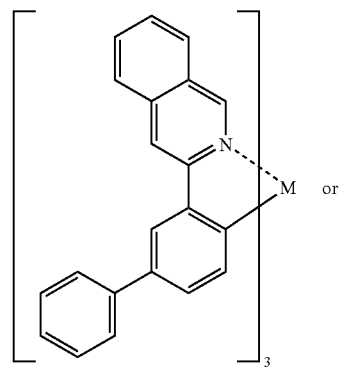
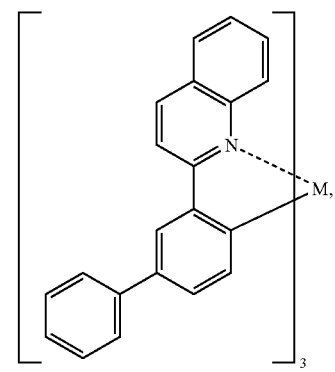
wherein M is a metal having an atomic weight greater than 40.
21. The device of claim 19, further comprising an electron transport layer disposed between the cathode and the emissive layer.